US012741143B2

(12) United States Patent
Zhang et al.

(10) Patent No.: US 12,741,143 B2
(45) Date of Patent: Sep. 22, 2026

(54) ELECTRIC STIMULATION METHOD BASED ON INSPIRATION OF HEALTHY SIDE LOWER LIMB MUSCLE SYNERGY AND SYSTEM THEREOF

(71) Applicant: Hangzhou Dianzi University, Hangzhou City (CN)

(72) Inventors: Jianhai Zhang, Hangzhou City (CN); Shikai Huang, Hangzhou City (CN); Shuai Hu, Hangzhou City (CN); Hua Ye, Hangzhou City (CN); Luzhou Zheng, Hangzhou City (CN)

(73) Assignee: Hangzhou Dianzi University, Hangzhou City (CN)

( * ) Notice: Subject to any disclaimer, the term of this patent is extended or adjusted under 35 U.S.C. 154(b) by 290 days.

(21) Appl. No.: 18/596,172

(22) Filed: Mar. 5, 2024

(65) Prior Publication Data

US 2025/0001174 A1 Jan. 2, 2025

(30) Foreign Application Priority Data

Jun. 29, 2023 (CN) ........................ 202310782596.4

(51) Int. Cl.
*A61N 1/36* (2006.01)

(52) U.S. Cl.
CPC ..... *A61N 1/36031* (2017.08); *A61N 1/36003* (2013.01)

(58) Field of Classification Search
CPC ............ A61N 1/36031; A61N 1/36003; A61N 1/0452
See application file for complete search history.

(56) References Cited

U.S. PATENT DOCUMENTS 8,165,685 B1 * 4/2012 Knutson ............ A61N 1/36034 607/2
9,498,623 B2 * 11/2016 Shimoda .............. A61B 5/1128
2010/0324699 A1 * 12/2010 Herr .......................... A61F 2/66 623/27
2021/0283001 A1 * 9/2021 Von Zitzewitz ....... A61B 5/112

FOREIGN PATENT DOCUMENTS

CN 205073522 U * 3/2016
CN 106492345 A * 3/2017 ......... A61N 1/36135
CN 115177864 A * 10/2022 ......... A61N 1/36014
CN 112870011 B * 1/2024 ........... A61H 1/0237

* cited by examiner

*Primary Examiner* — Michael J Lau
(74) *Attorney, Agent, or Firm* — Ryan T. Grace; Advent, LLP

(57) ABSTRACT

An electric stimulation method based on inspiration of healthy side lower limb muscle synergy and a system thereof are provided. A motion process of a healthy side limb of an individual is analyzed, and in combination with an electromyographic signal and a motion posture signal, a muscle motion model which is more in line with coordination of an individual's own limb is established, and the healthy side limb muscle motion model is used to guide the affected limb to move. Inspired by the healthy side limb of an individual, the electromyographic signal and the motion posture signal of the healthy side limb are acquired, and the motion model of the healthy side limb is established. The change relationship of the muscle synergy activation degree with the time is mapped as the change relationship of the muscle synergy activation degree with the angle, which eliminates time-varying interference.

20 Claims, 4 Drawing Sheets

ELECTRIC STIMULATION METHOD BASED ON INSPIRATION OF HEALTHY SIDE LOWER LIMB MUSCLE SYNERGY AND SYSTEM THEREOF

CROSS-REFERENCE TO RELATED APPLICATION

This patent application claims the benefit and priority of Chinese Patent Application No. 202310782596.4 filed with the China National Intellectual Property Administration on Jun. 29, 2023, the disclosure of which is incorporated by reference herein in its entirety as part of the present application.

TECHNICAL FIELD

The present disclosure belongs to the technical field of signal processing, and more specifically relates to an electric stimulation method based on inspiration of healthy side lower limb muscle synergy and a system thereof.

BACKGROUND

Stroke is a neurological disorder disease, which will lead to unilateral side limb dyskinesia of an individual, thus seriously affecting the daily life ability of an individual. Some studies show that the symmetry of lower limbs is very important for maintaining body balance and stability, and it is also closely related to athletic ability. It has been studied that the electric stimulation method under a suitable model can promote the recovery of muscle activity ability of an individual. Therefore, a modelling method of a lower limb motion suitable for the individual himself/herself is very important.

At present, there are several modeling methods for lower limb motion. A modeling method based on machine learning analyzes and processes a large number of kinematic and physiological data through the machine learning technology to establish a muscle model. A modeling method based on a medical imaging technology obtains internal structure information of human lower limbs by the medical imaging technology such as magnetic resonance imaging and computed tomography, and a three-dimensional muscle model is established.

The above-mentioned modeling methods have the following problems. The modeling method based on the medical imaging technology is too expensive and difficult to implement. The modeling method based on massive data ignores the characteristics of the differences between movement patterns of different individuals. The electric stimulation method based on this modeling method may not be suitable for the individual's own specificity and violate the individual's own coordination, thereby resulting in the failure to achieve the best muscle activation effect.

SUMMARY

Aiming at the shortcomings of the above-mentioned modeling methods, the present disclosure provides a modeling method based on inspiration of healthy side lower limb muscle synergy and a system thereof. According to the present disclosure, a motion process of a healthy side limb of an individual is analyzed, and in combination with an electromyographic signal and a motion posture signal, a muscle motion model which is more in line with coordination of an individual's own limb is established, and the healthy side limb muscle motion model is used to guide the affected limb to move.

In order to achieve the above-mentioned object, in a first aspect, the present disclosure provides an electric stimulation method based on inspiration of healthy side lower limb muscle synergy, including the following steps:

- S1, acquiring a surface electromyographic signal and a motion posture signal of a healthy side limb of an individual during an action period; preprocessing the signals and segmenting the signals according to a motion segment to obtain a set of electromyographic signal data and a set of motion posture data;
- S2, analyzing, by using a muscle synchronous synergy extraction algorithm, the obtained electromyographic signal of the healthy side limb to obtain a synergy relationship between muscles of the healthy side limb as a motion model of the healthy side limb of the same individual;
- S3, fitting, for the motion posture data, an angle signal and a motion speed signal in a motion process to obtain a muscle synergy pattern, and mapping the obtained muscle synergy pattern to a stable angle space for avoiding time-varying influence, as a motion guidance model of the affected limb of the same individual; and
- S4, setting a maximum motion angle and a motion speed parameter of a lower limb rehabilitation instrument, and setting a stimulation parameter and starting time of an electric stimulator based on the motion guidance model.

In a second aspect, the present disclosure provides an electric stimulation control system based on inspiration of healthy side lower limb muscle synergy, including:

- a data acquiring and preprocessing module, configured to acquire a surface electromyographic signal and a motion posture signal of a healthy side limb of an individual during an action period; preprocess the signals and segment the signals according to a motion segment to obtain a set of electromyographic signal data and a set of motion posture data;
- a healthy-side-limb motion model constructing module, configured to analyze, by using a muscle synchronous synergy extraction algorithm, the obtained electromyographic signal of the healthy side limb to obtain a synergy relationship between muscles of the healthy side limb as a motion model of the healthy side limb of the same individual;
- an affected-limb motion model constructing module, configured to fit, for the motion posture data, an angle signal and a motion speed signal in a motion process to obtain a muscle synergy pattern, and map the obtained muscle synergy pattern to a stable angle space for avoiding time-varying influence as a motion guidance model of the affected limb of the same individual; and
- an electric stimulation controlling module, configured to set a maximum motion angle and a motion speed parameter of a lower limb rehabilitation instrument in a lower limb rehabilitation system, and set a stimulation parameter and starting time of an electric stimulator based on the motion model of an affected limb.

In a third aspect, the present disclosure provides an electronic device including a processor and a memory, where the memory stores machine-executable instructions capable of being executed by the processor, and the processor executes the machine-executable instructions to implement the method or the system.

In a fourth aspect, the present disclosure provides a non-transitory machine-readable storage medium, where the machine-readable storage medium stores machine-executable instructions, which, when being called and executed by a processor, cause the processor to implement the method or the system.

The present disclosure has the following beneficial effect.

Compared with the background, in order to solve the problem of individual dyskinesia, inspired by the healthy side limb of an individual, the present disclosure acquires the electromyographic signal and the motion posture signal of the healthy side limb, and establishes the motion model of the healthy side limb. The change relationship of the muscle synergy activation degree with the time is mapped as the change relationship of the muscle synergy activation degree with the angle, which eliminates time-varying interference, such that an electric stimulator can apply electric stimulation with the change of angle, thereby achieving a more accurate stimulation effect.

According to the inspiration guidance of the healthy side of the individual, and with the help of an internal mechanism of bilateral side limb symmetry, the present disclosure deeply analyzes the relationship between the motion posture and the motion electromyographic signal, and establishes a muscle motion model more suitable for the affected limb, which is more in line with coordination of an individual's own limb.

The present disclosure provides a method of converting the change relationship of the muscle activation degree with time into the change relationship of the muscle activation degree with the angle, which can apply corresponding electric stimulation at different motion stages more accurately and avoid the time-varying influence.

BRIEF DESCRIPTION OF THE DRAWINGS

In order to explain the embodiments of the present disclosure or the technical scheme in the prior art more clearly, the drawings needed in the embodiments will be briefly introduced hereinafter. Apparently, the drawings described below are only some embodiments of the present disclosure, and other drawings can be obtained according to these drawings without creative work for those skilled in the art.

FIG. 2A-FIG. 2F are analytical diagrams of healthy side limb muscle synergy according to an embodiment of the present disclosure; in which FIG. 2A shows the weight ratio of muscles in the first synergy pattern; FIG. 2B shows the activation degree of the first synergy pattern changing with time; FIG. 2C shows the weight ratio of muscles in the second synergy pattern; FIG. 2D shows the activation degree of the second synergy pattern changing with time; FIG. 2E shows the weight ratio of muscles in the third synergy pattern; FIG. 2F shows the activation degree of the third synergy pattern changing with time.

FIG. 3A-FIG. 3C are graphs showing the relationship of an activation degree of a muscle synergy structure changing with the angle according to an embodiment of the present disclosure; in which FIG. 3A shows the activation degree of the first synergy pattern changing with the angle; FIG. 3B shows the activation degree of the second synergy pattern changing with angle; FIG. 3C shows the activation degree of the third synergy pattern changing with the angle.

DETAILED DESCRIPTION OF THE EMBODIMENTS

A plurality of exemplary embodiments of the present disclosure will now be described in detail. This detailed description should not be considered as a limitation of the present disclosure, but should be understood as a more detailed description of certain aspects, characteristics and embodiments of the present disclosure.

It should be understood that the term described in the present disclosure is only for describing specific embodiments and is not used to limit the present disclosure. In addition, it should be understood that each intermediate value between the upper limit and the lower limit of the numerical range in the present disclosure is also specifically disclosed. Every smaller range between the intermediate value within any stated value or stated range and any other stated value or the intermediate value within the stated range is also included in the present disclosure. The upper limit and the lower limit of these smaller ranges can be independently included in or excluded from the range.

It is obvious to those skilled in the art that many improvements and changes can be made to the detailed description of the present disclosure without departing from the scope or spirit of the present disclosure. Other embodiments obtained from the description of the present disclosure will be apparent to those skilled in the art. The specification and the embodiments of the present disclosure are only exemplary.

Figure 1:
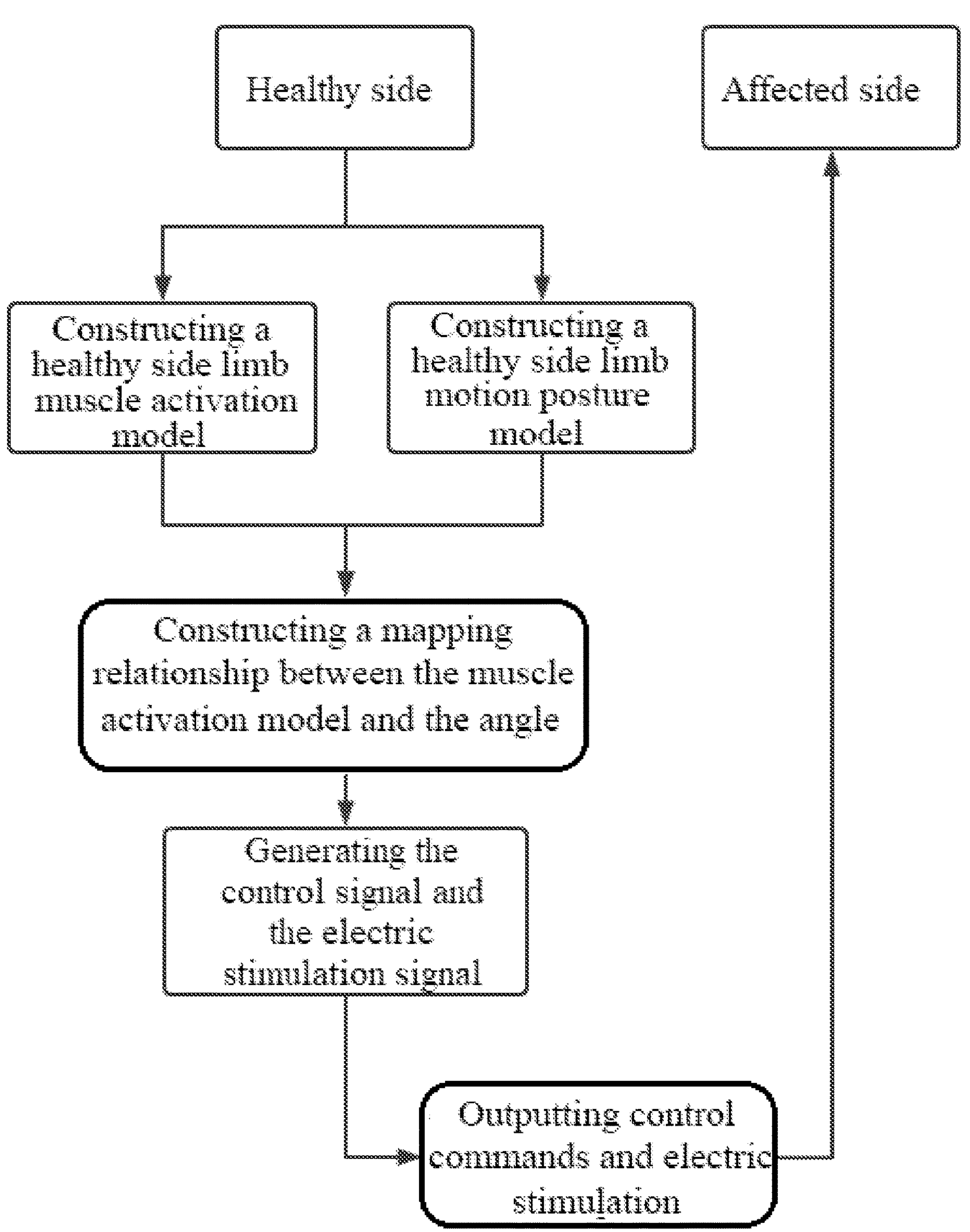
FIG. 1 is a modeling method and a rehabilitation system inspired by a healthy side limb according to an embodiment of the present disclosure.
Figures 2A, 2B, 2C, 2D, 2E, 2F:
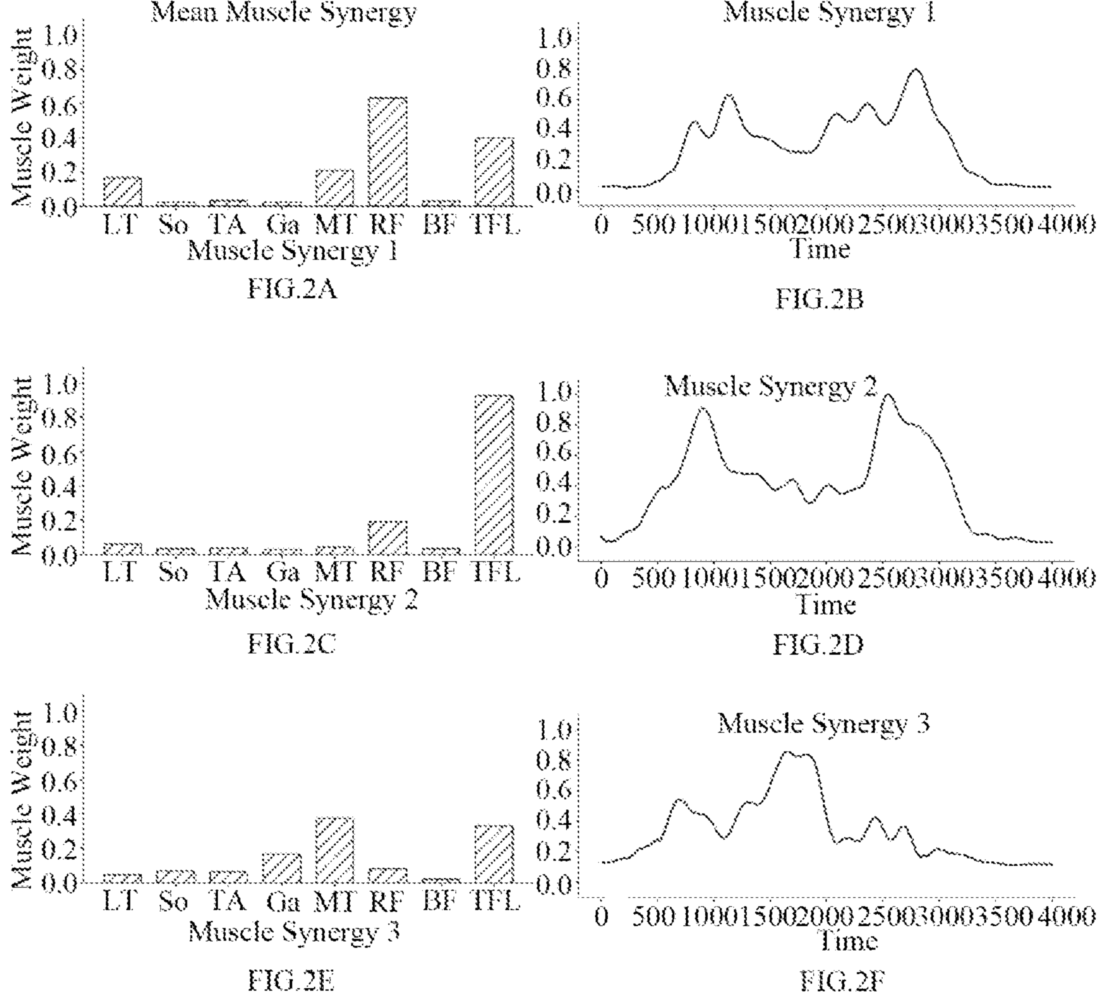

The present disclosure provides an electric stimulation method based on inspiration of healthy side lower limb muscle synergy. The method has the following flow as shown in FIG. 1, including the following steps S1 to S4.

In step S1, a surface electromyographic signal and a motion posture signal of a healthy side limb of an individual during an action period are acquired, the signals are preprocessed and segmented according to a motion segment to obtain a set of electromyographic signal data and a set of motion posture data.

In step S2, a muscle synchronous synergy extraction algorithm is adopted to analyze the obtained electromyographic signal of the healthy side limb to obtain a synergy relationship between the muscles of the healthy side limb as a motion model of the healthy side limb of the same individual.

In step S3, for the motion posture data, an angle signal and a motion speed signal in a motion process are fitted to obtain muscle synergy pattern, and the obtained muscle synergy pattern is mapped to a stable angle space for avoiding time-varying influence, as a motion guidance model of the affected side limb of the same individual.

In step S4, based on the motion guidance model, a maximum motion angle and a motion speed parameter of a lower limb rehabilitation instrument are set, and a stimulation parameter and starting time of an electric stimulator are set.

Further, the Step S1 specifically includes the following steps S1.1 to S1.2.

In step S1.1, the step of preprocessing the electromyographic signal is as follows: first, performing power frequency removal filtering on the acquired original electromyographic signal of the healthy side limb, then performing band-pass filtering on the electromyographic signal, thereafter, performing rectification processing on the electromyographic signal, and finally performing low-pass filtering, so as to obtain an electromyographic signal envelope.

Further, a filter of 50 Hz is selected to remove the power frequency interference in the electromyographic signal, a 6-order Butterworth filter of 50 to 450 Hz is selected to perform band-pass filtering on the electromyographic signal, and a 6-order Butterworth filter of 4 Hz is selected to perform low-pass filtering.

In step S1.2, the step of preprocessing the motion posture signal is as follows: analyzing the acquired motion posture data of the healthy side limb, segmenting the signal according to the motion segment, and extracting motion angle information and motion speed information of the lower limb from the motion posture data.

Further, the Step S2 specifically includes a step S2.1.

In step S2.1, maximum normalization processing on the electromyographic signal envelope of the healthy side limb, and obtaining a muscle synchronization synergy relationship model in time domain by a non-negative matrix decomposition algorithm.

Further, the Step S2.1 specifically includes:

integrating the electromyographic signal data of various channels into an m×n matrix;

$$V=(v_{mn}) \tag{1}$$

where m represents a number of channels of a selected electromyographic signal, and n represents a number of sampling points of the electromyographic signal in a motion period;

initializing two matrices randomly, namely, a muscle weight matrix W and an activation degree matrix H, and both matrices being non-negative:

$$\begin{cases} W \geq 0 \\ H \geq 0 \end{cases} \tag{2}$$

where the matrix W has m rows and r columns, the matrix H has r rows and n columns, and r represents a number of muscle synergies;

defining R as an error distance between a reconstructed matrix after decomposition and an original matrix:

$$R=\min_{W,H}\|V-WH\|^2 \tag{3}$$

performing iteration on two matrices W and H by using a gradient descent method:

$$W_{ik} \leftarrow W_{ik}\frac{(VH^T)_{ik}}{(WHH^T)_{ik}} \tag{4}$$

$$H_{kj} \leftarrow H_{kj}\frac{(W^TH)_{kj}}{(W^TWH)_{kj}} \tag{5}$$

where i has a range of [1,m], j has a range of [1,n], and k has a range of [1, r];

when the error distance R is less than a threshold or the number of iterations reaches a maximum number of iterations, ending the iteration.

In an embodiment, $10^{-5}$ is selected as the threshold of the error distance, and 2000 is selected as the maximum number of iterations.

The matrix W obtained at the end of the iteration represents the muscle weight matrix in the synergy relationship, and the matrix H represents the activation degree matrix in the synergy relationship.

The number r of muscle synergies is determined by a difference VAF between a reconstructed matrix Vr and an original matrix V:

$$V_r=WH \tag{6}$$

$$VAF=1-\frac{\sum_{i,j}(V-V_r)^2_{i,j}}{\sum_{i,j}V^2_{i,j}} \tag{7}$$

where i has a range of [1, m] and j has a range of [1, n].

When an average value of the VAF in each motion period is greater than a set threshold, r is determined as the current number of muscle synergies;

In an embodiment, 0.92 is selected as the set threshold.

The maximum normalization is performed on the analyzed matrix W, and then the similarity of the matrix W in each period is analyzed by using a correlation coefficient p, in which the formula is:

$$p(W1,W2)=\frac{r\sum_{c=1}^{r}W1_cW2_c-\sum_{c=1}^{r}W1_c\sum_{c=1}^{r}W2_c}{\sqrt{r\sum_{c=1}^{r}W1_c^2-\left(\sum_{c=1}^{r}W1_c\right)^2}\sqrt{r\sum_{c=1}^{r}W2_c^2-\left(\sum_{c=1}^{r}W2_c\right)^2}} \tag{8}$$

where W1 and W2 represent the muscle weight matrices W for two different action periods, respectively, c represents a column in the corresponding matrix W with the range of [1,r], a plurality of matrices are selected by comparing the correlation coefficient p for averaging to obtain a weight ratio relationship of a plurality of muscles of the healthy side limb under different synergy patterns. Table 1 shows the correlation degree for different periods in all motion periods.

TABLE 1

Correlation degree of synergy matrices during each period

| | W1 | W2 | W3 | W4 | W5 | W6 | W7 | W8 |
|---|---|---|---|---|---|---|---|---|
| W1 | 1 | 0.9479 | 0.9534 | 0.9611 | 0.523 | 0.8277 | 0.4245 | 0.6215 |
| W2 | 0 | 1 | 0.9874 | 0.9695 | 0.6519 | 0.9118 | 0.4755 | 0.7384 |
| W3 | 0 | 0 | 1 | 0.9728 | 0.6721 | 0.9015 | 0.3717 | 0.7558 |
| W4 | 0 | 0 | 0 | 1 | 0.608 | 0.851 | 0.4296 | 0.6759 |
| W5 | 0 | 0 | 0 | 0 | 1 | 0.722 | 0.1587 | 0.9683 |
| W6 | 0 | 0 | 0 | 0 | 0 | 1 | 0.4736 | 0.7926 |
| W7 | 0 | 0 | 0 | 0 | 0 | 0 | 1 | 0.18 |
| W8 | 0 | 0 | 0 | 0 | 0 | 0 | 0 | 1 |

The motion period with the correlation coefficient p>0.8 is averaged to obtain the weight, so as to obtain the proportional relationship among eight muscles (vastus lateralis muscle, medial vastus muscle, rectus femoris, tensor fascia latae, biceps femoris musle, musculi adductor longus, gastrocnemius muscle and tibialis anterior muscle) in r muscle synergy patterns.

Maximum normalization is performed on the analyzed activation degree matrix H.

FIG. 2A-FIG. 2F are analytical diagrams (r=3) of healthy side limb muscle synergy according to an embodiment of the present disclosure.

Figure 3A:
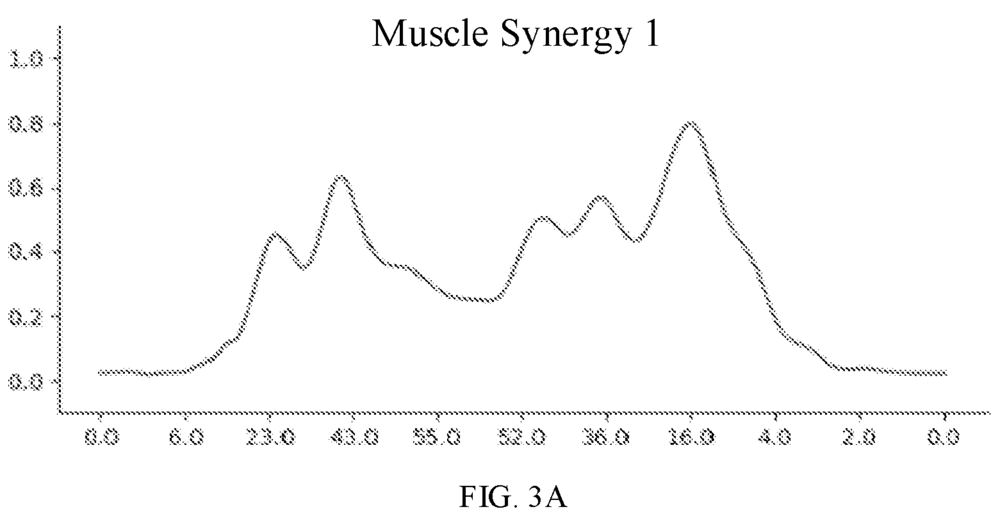
Figure 3B:
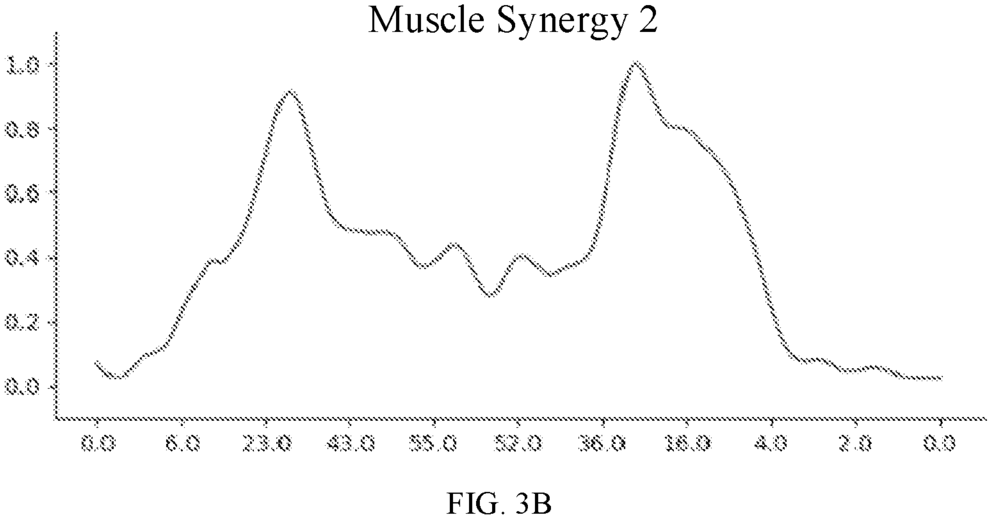
Figure 3C:
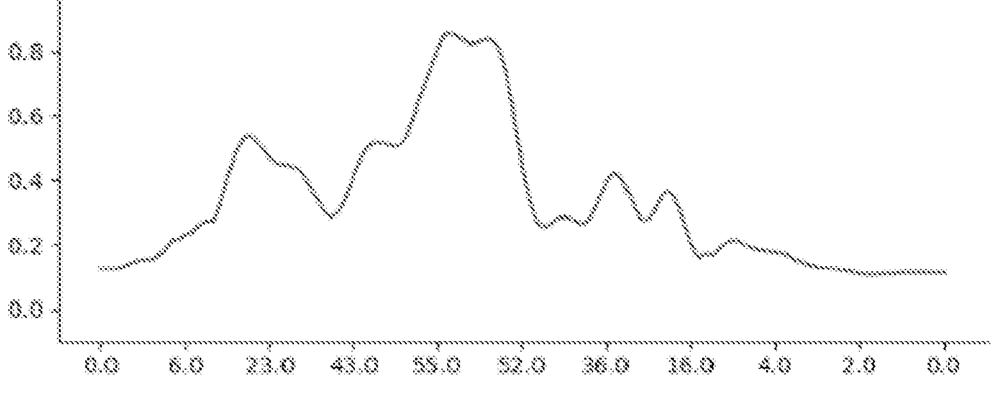

As shown in FIG. 3A-FIG. 3C, the synergy relationship of healthy side limb muscles (r=3) and the muscle activation degree changing with time are obtained.

Further, the Step S3 specifically includes steps S3.1 to S3.5.

In step S3.1, the signal which changes with time is fitted with respect to the extracted angle signal.

further, Step S3.1 includes preprocessing an original angle signal of the healthy side limb to eliminate possible noises and abnormal values, then constructing a fitting function θ(t) to indicate a fitting relationship between the angle and time, and selecting an appropriate period to fit the angle signal, in which the specific formula is as follows:

$$\theta(t) = a_1 \sin(\omega t) + b_1 \tag{9}$$

where $a_1$ and $b_1$ are constants to be solved, t is time, and ω is angular frequency; and $$\omega = \frac{\pi}{60}$$

A least square method is used to estimate parameters of the fitting function θ(t), and an error $S_1$ between an actual data and the fitting function θ(t) is minimized by optimizing the values of $a_1$ and $b_1$, in which the specific formula is as follows:

$$S_1 = \sum_{i=1}^{n} (y_i - a_1 \sin(\omega t_i) + b_1)^2 \tag{10}$$

where $y_i$ represents the actual value of the angle signal, and i represents a sampling point in the range of [1,n].

In step S3.2, the signal which changes with time is fitted with respect to the extracted angular velocity signal.

Specifically, the Step S3.2 includes preprocessing an original angular velocity signal of the healthy side limb to eliminate possible noises and abnormal values, then constructing a fitting function $\theta_1(t)$ to indicate a fitting relationship between angular velocity and time, and selecting an appropriate period to fit the angular velocity signal, in which the specific formula is as follows:

$$\theta_1(t) = a_2 \sin(\omega t) + b_2 \tag{11}$$

where $a_2$ and $b_2$ are constants to be solved, t is time, and ω is angular frequency; and $$\omega = \frac{\pi}{60}$$

is selected as the angular frequency.

A least square method is used to estimate parameters of the fitting function $\theta_1$, and an error $S_2$ between an actual data and the fitting function $\theta_1$ is minimized by optimizing the values of $a_2$ and $b_2$, in which the specific formula is as follows:

$$S_2 = \sum_{i=1}^{n} (y'_i - a_2 \sin(\omega t) + b_2)^2 \tag{12}$$

where $y'_i$ represents an actual value of the angular velocity signal, and i represents a sampling point in the range of [1,n].

In step S3.3, according to the characteristic that a muscle activation degree curve has a plurality of peaks, a Gaussian distribution model is adopted to fit the curve to obtain a fitting relationship G(h) between the activation degree and time, in which the formula is as follows:

$$G(h) = \sum_{i=1}^{k} \omega_i \phi(t; \mu_i, \sigma_i^2) \tag{13}$$

where t corresponds to an abscissa in the muscle activation degree, k represents a number of Gaussian distributions, $\omega_i$ represents a weight of an i-th Gaussian distribution, $\phi(h; \mu_i, \sigma_i^2)$ represents a probability density function of the Gaussian distribution, $\mu_i$ represents a mean value of the i-th Gaussian distribution, and $\sigma_i^2$ represents a variance of the i-th Gaussian distribution; when fitting is performed by using the Gaussian distribution model, the maximum likelihood estimation method is used to solve each parameter, to obtain the optimal fitting result.

In step S3.4, according to the relationship θ(t) between the angle and time obtained in S3.1 and the relationship G(t) between the activation degree and time obtained in S3.3, a mapping relationship between the activation degree and the angle is constructed.

Further, first, a derivative of θ(t) and G(t) is calculated to obtain θ'(t) and G'(t), and then a corresponding relationship G(θ) between the activation signal and the angle is obtained:

$$\frac{dG}{d\theta} = \frac{dG}{dt} \cdot \frac{dt}{d\theta} = \frac{G'(t)}{\theta'(t)} \tag{14}$$

$$G(\theta) = \int \frac{G'(t)}{\theta'(t)} dt \tag{15}$$

Because a sampling frequency of the angle is lower than that of the signal, linear interpolation is performed on angle sampling to match the angle sampling with signal sampling frequency.

In step S3.5, in the relationship G(θ), a corresponding angle range in which the activation signal is greater than the activation threshold α is selected as an angle range $\theta_r$ in which the muscle synergy pattern is activated.

The threshold α at which the synergy pattern is activated is 0.5.

Further, the Step S4 specifically includes steps S4.1 to S4.5.

In step S4.1, according to the angle signal fitting function θ(t) obtained in S3.1, a maximum angle value of the healthy side limb is obtained in different motion periods, and the maximum motion angle of the lower limb rehabilitation instrument is set.

In step S4.2, according to the angular velocity signal fitting function $\theta_1(t)$ obtained in S3.2, a motion speed and a motion period of the lower limb rehabilitation instrument are set, such that the lower limb rehabilitation instrument works according to the motion model of the healthy side limb of the same individual;

In step S4.3, a frequency and a pulse width of the electric stimulator in the lower limb rehabilitation system are set.

A lowest frequency capable of activating lower limb muscles of an individual is selected as a stimulation frequency of the electric stimulator, and 50 μs is selected as a pulse width of the electric stimulator.

In step S4.4, proportions of an electric stimulation intensities of various channels of the electric stimulator are set, muscle M with a maximum weight in the muscle weight matrix W is set to adopt a maximum stimulation intensity according to the muscle weight matrix W obtained in Step S2, and stimulation intensities of the other muscles are set one by one according to formula (16):

$$\frac{S_M}{S_i} = \frac{W_M}{W_i}, \tag{16}$$

where $S_M$ represents a stimulation intensity of the muscle M; $S_i$ represents a stimulation intensity of a muscle i, in which i≠M; $W_M$ represents a muscle weight of the muscle M; and $W_i$ represents a muscle weight of the muscle i.

In step S4.5, according to the corresponding relationship G(θ) between the muscle activation degree and the angle obtain in S3.4, when the motion angle falls within the angle range $\theta_r$ in which the synergy pattern is activated during the operation of the low limb rehabilitation instrument, the electric stimulator with set parameters are started. The electric stimulator continuously works, and when the motion angle does not fall within the angle range $\theta_r$ in which the muscle synergy pattern is activated, the electric stimulator is stopped.

Figure 4:
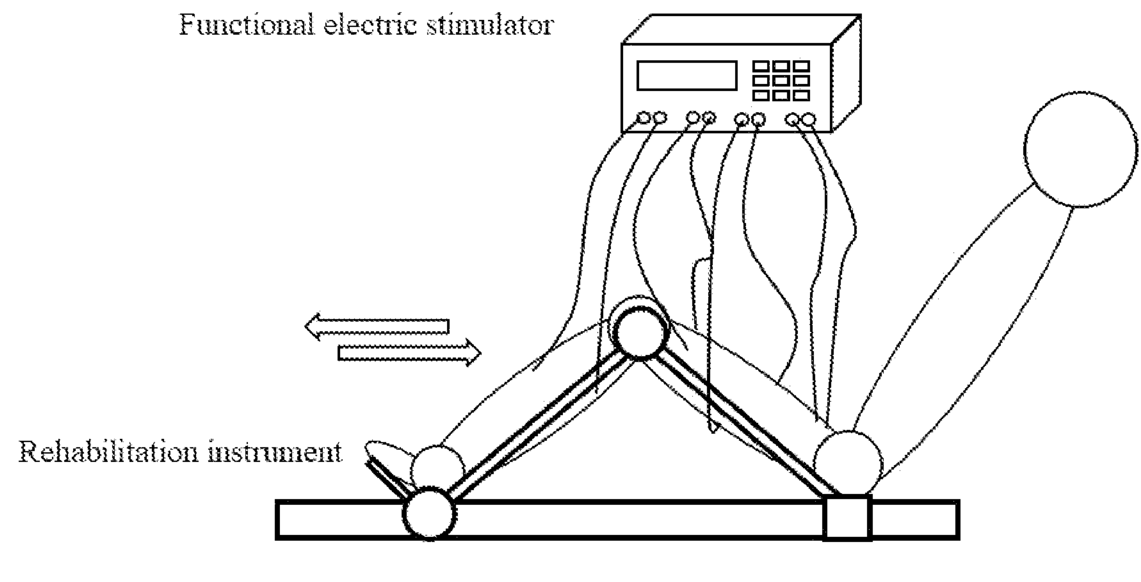
FIG. 4 is a schematic diagram of a lower limb rehabilitation system according to an embodiment of the present disclosure.

8 control points of the electric stimulator are selected, which are corresponding to vastus lateralis muscle, medial vastus muscle, rectus femoris, tensor fascia latae, biceps femoris musle, musculi adductor longus, gastrocnemius muscle and tibialis anterior muscle of the lower limbs, respectively. Electric stimulation is applied to the affected muscles as shown in FIG. 4.

What is claimed is:

1. An electric stimulation method based on inspiration of healthy side lower limb muscle synergy, comprising following steps:

S1, acquiring a surface electromyographic signal and a motion posture signal of a healthy side limb of an individual during an action period; preprocessing the signals and segmenting the signals according to a motion segments of the action period to obtain a set of electromyographic signal data and a set of motion posture data;

S2, analyzing, by using a muscle synchronous synergy extraction algorithm, the obtained electromyographic signal data of the healthy side limb to obtain a muscle synergy pattern between muscles of the healthy side limb;

S3, fitting, for the motion posture data, an angle signal and a motion speed signal in a motion process as a motion model of the healthy side limb of the same individual, and mapping the obtained muscle synergy pattern to a stable angle space for avoiding time-varying influence, to obtain a motion guidance model of the affected limb of the same individual; and

S4, setting, according to the motion guidance model, a maximum motion angle, a motion speed, and a motion period of a lower limb rehabilitation instrument connected to the individual, and setting, according to the motion guidance model, proportions of electric stimulation intensities of channels of an electric stimulator, which is contained in the lower limb rehabilitation instrument and has control points attached to skin surface of affected side lower limb muscles of the individual, and an angle range for starting the electric stimulator, such that during the low limb rehabilitation instrument being working according to the motion model of the healthy side limb of the individual, the electric stimulator is started when a motion angle of the low limb rehabilitation instrument falls within the angle range in which the muscle synergy pattern is activated, and when the motion angle does not fall within the angle range, the electric stimulator is stopped.

2. The method according to claim 1, wherein the preprocessing the surface electromyographic signal in Step S1 is as follows: performing power frequency removal filtering, band-pass filtering, rectification processing and low-pass filtering on the acquired surface electromyographic signal in sequence to obtain an electromyographic signal envelope.

3. The method according to claim 1, wherein the preprocessing the motion posture signal in Step S1 is as follows: analyzing the acquired motion posture signal, segmenting the signal according to the motion segments, and extracting motion angle information and motion speed information of a lower limb.

4. The method according to claim 1, wherein the Step S2 comprises:

performing maximum normalization processing on the electromyographic signal envelope of the healthy side limb, and obtaining the muscle synergy pattern in time domain by a non-negative matrix decomposition algorithm; comprising:

integrating the electromyographic signal data of respective channels into an m×n matrix;

$$V = (v_{mn}) \tag{1}$$

where m represents a number of channels of a selected electromyographic signal, and n represents a number of sampling points of the electromyographic signal in a motion period;

randomly initializing two matrices of a muscle weight matrix W and an activation degree matrix H, wherein both matrices need to be non-negative:

$$\begin{cases} W \geq 0 \\ H \geq 0 \end{cases} \tag{2}$$

where the matrix W has m rows and r columns, the matrix H has r rows and n columns, and r represents a number of muscle synergies;

defining R as an error distance between a reconstructed matrix after decomposition and an original matrix:

$$R = \min_{W,H}\|V - WH\|^2 \tag{3}$$

performing iteration on two matrices W and H by using a gradient descent method:

$$W_{ik} \leftarrow W_{ik}\frac{(VH^T)_{ik}}{(WHH^T)_{ik}} \tag{4}$$

$$H_{kj} \leftarrow H_{kj}\frac{(W^T H)_{kj}}{(W^T WH)_{kj}} \tag{5}$$

where i has a range of [1,m], j has a range of [1,n], and k has a range of [1, r];

ending the iteration, when the error distance R is less than a threshold or the number of iterations reaches a maximum iteration number, wherein the matrix W obtained at the end of the iteration represents the muscle weight matrix in the muscle synergy pattern, and the matrix H represents the activation degree matrix in the muscle synergy pattern;

the number r of muscle synergies is determined by a difference VAF between a reconstructed matrix Vr and an original matrix V:

$$V_r = WH \tag{6}$$

$$VAF = 1 - \frac{\sum_{i,j}(V - V_r)_{i,j}^2}{\sum_{i,j}V_{i,j}^2} \tag{7}$$

when an average value of the VAF in each motion period is greater than a set threshold, r is determined as a current number of muscle synergies; and performing maximum normalization on the analyzed matrix W, and analyzing similarity of the matrix W in each period by using a correlation coefficient p, which is expressed as:

$$p(W1, W2) = \frac{r\sum_{c=1}^{r} W1_c W2_c - \sum_{c=1}^{r} W1_c \sum_{c=1}^{r} W2_c}{\sqrt{r\sum_{c=1}^{r} W1_c^2 - \left(\sum_{c=1}^{r} W1_c\right)^2}\sqrt{r\sum_{c=1}^{r} W2_c^2 - \left(\sum_{c=1}^{r} W2_c\right)^2}} \tag{8}$$

where W1 and W2 represent muscle weight matrices W for two different action periods, respectively, c represents a column in the corresponding matrix W with a range of [1,r], a plurality of matrices are selected by comparing the correlation coefficient p for averaging, to obtain a weight ratio relationship of a plurality of muscles of the healthy side limb under different muscle synergy patterns;

performing maximum normalization on analyzed activation degree matrix H.

5. The method according to claim 4, wherein the Step S3 comprises:

S3.1: fitting the signal which changes with time with respect to the extracted angle signal, comprising:

preprocessing an original angle signal of the healthy side limb to eliminate possible noises and abnormal values, constructing a fitting function θ(t) to indicate a fitting relationship between the angle and time, and selecting an appropriate period to fit the angle signal, which is expressed as follows:

$$\theta(t) = a_1\sin(\omega t) + b_1 \tag{9}$$

where $a_1$ and $b_1$ are constants to be solved, t is time, and ω is angular frequency;

using a least square method to estimate parameters of the fitting function θ(t), and minimizing an error $S_1$ between an actual value and the fitting function θ(t) by optimizing values of $a_1$ and $b_1$, which is expressed as follows:

$$S_1 = \sum_{i=1}^{n}(y_i - a_1\sin(\omega t_i) + b_1)^2 \tag{10}$$

where $y_i$ represents the actual value of the angle signal;

S3.2: fitting the signal which changes with time with respect to the extracted angular velocity signal, comprising:

preprocessing an original angular velocity signal of the healthy side limb to eliminate possible noises and abnormal values, constructing a fitting function $\theta_1(t)$ to indicate a fitting relationship between angular velocity and time, and selecting an appropriate period to fit the angular velocity signal, which is expressed as follows:

$$\theta_1(t) = a_2\sin(\omega t) + b_2 \tag{11}$$

where $a_2$ and $b_2$ are constants to be solved, t is time, and ω is angular frequency;

using a least square method to estimate parameters of the fitting function $\theta_1$, and minimizing an error $S_2$ between an actual value and the fitting function $\theta_1$ by optimizing values of $a_2$ and $b_2$, which is expressed as follows:

$$S_2 = \sum_{i=1}^{n}(y_i' - a_2\sin(\omega t) + b_2)^2 \tag{12}$$

where $y'_i$ represents an actual value of the angular velocity signal, and i represents a sampling point in a range of [1,n];

S3.3: according to characteristic that a muscle activation degree curve has a plurality of peaks, using a Gaussian distribution model to fit the curve to obtain a fitting relationship G(h) between the activation degree and time, which is expressed as follows:

$$G(h) = \sum_{i=1}^{k}\omega_i\phi(t; \mu_i, \sigma_i^2) \tag{13}$$

where t corresponds to an abscissa in the muscle activation degree, k represents a number of Gaussian distributions, $\omega_i$ represents a weight of an i-th Gaussian distribution, $\phi(h; \mu_i, \sigma_i^2)$ represents a probability density function of the Gaussian distribution, $\mu_i$ represents a mean value of the i-th Gaussian distribution, and $\sigma_i^2$ represents a variance of the i-th Gaussian distribution;

S3.4: according to the relationship θ(t) between the angle and time obtained in S3.1 and the relationship G(t) between the activation degree and time obtained in S3.3, constructing a mapping relationship between the activation degree and the angle;

calculating a derivative of θ(t) and G(t) to obtain θ'(t) and G'(t), and obtaining a corresponding relationship G(θ) between the activation signal and the angle:

$$\frac{dG}{d\theta} = \frac{dG}{dt} \cdot \frac{dt}{d\theta} = \frac{G'(t)}{\theta'(t)} \tag{14}$$

$$G(\theta) = \int \frac{G'(t)}{\theta'(t)} dt \tag{15}$$

performing linear interpolation on angle sampling to match the angle sampling with signal sampling frequency, considering that a sampling frequency of the angle is lower than that of the signal;

S3.5: in the relationship G(θ), selecting a corresponding angle range in which the activation signal is greater than the activation threshold a as an angle range $\theta_r$ in which the muscle synergy pattern is activated.

6. The method according to claim 5, wherein the Step S4 comprises:

S4.1: according to the angle signal fitting function θ(t) obtained in S3.1, solving a maximum angle value of the healthy side limb in different motion periods, and setting the maximum motion angle of the lower limb rehabilitation instrument;

S4.2: according to the angular velocity signal fitting function $\theta_1(t)$ obtained in S3.2, setting a motion speed and a motion period of the lower limb rehabilitation instrument, such that the lower limb rehabilitation instrument works according to the motion model of the healthy side limb of the same individual;

S4.3: setting a frequency and a pulse width of the electric stimulator;

S4.4, setting proportions of electric stimulation intensities of channels of the electric stimulator, setting muscle M with a maximum weight in the muscle weight matrix W to have a maximum stimulation intensity according to the muscle weight matrix W obtained in Step S2, and setting stimulation intensities of other muscles one by one according to formula (16);

$$\frac{S_M}{S_i} = \frac{W_M}{W_i} \tag{16}$$

where $S_M$ represents a stimulation intensity of the muscle M; $S_i$ represents a stimulation intensity of a muscle i, in which i≠M; $W_M$ represents a muscle weight of the muscle M; $W_i$ represents a muscle weight of the muscle i;

S4.5: according to the corresponding relationship G(θ) between the muscle activation degree and the angle obtain in S3.4, starting the electric stimulator with set parameters when the motion angle falls within the angle range $\theta_r$ in which the muscle synergy pattern is activated during operation of the low limb rehabilitation instrument, wherein the electric stimulator continuously works, and when the motion angle does not fall within the angle range $\theta_r$ in which the muscle synergy pattern is activated, the electric stimulator is stopped.

7. The method according to claim 6, wherein the Step S4.3 comprises selecting a lowest frequency capable of activating lower limb muscles of the individual as a stimulation frequency of the electric stimulator, and selecting 50 μs as a pulse width of the electric stimulator.

8. An electronic device, comprising a processor and a memory, wherein the memory stores machine-executable instructions capable of being executed by the processor, and the processor executes the machine-executable instructions to implement the method according to claim 1.

9. The electronic device according to claim 8, wherein the preprocessing the surface electromyographic signal in Step S1 is as follows: performing power frequency removal filtering, band-pass filtering, rectification processing and low-pass filtering on the acquired surface electromyographic signal in sequence to obtain an electromyographic signal envelope.

10. The electronic device according to claim 8, wherein the preprocessing the motion posture signal in Step S1 is as follows: analyzing the acquired motion posture signal, segmenting the signal according to the motion segments, and extracting motion angle information and motion speed information of a lower limb.

11. The electronic device according to claim 8, wherein the Step S2 comprises:

performing maximum normalization processing on the electromyographic signal envelope of the healthy side limb, and obtaining the muscle synergy pattern in time domain by a non-negative matrix decomposition algorithm; comprising:

integrating the electromyographic signal data of respective channels into an m×n matrix;

$$V = (v_{mn}) \tag{1}$$

where m represents a number of channels of a selected electromyographic signal, and n represents a number of sampling points of the electromyographic signal in a motion period;

randomly initializing two matrices of a muscle weight matrix W and an activation degree matrix H, wherein both matrices need to be non-negative:

$$\begin{cases} W \geq 0 \\ H \geq 0 \end{cases} \tag{2}$$

where the matrix W has m rows and r columns, the matrix H has r rows and n columns, and r represents a number of muscle synergies;

defining R as an error distance between a reconstructed matrix after decomposition and an original matrix:

$$R = \min_{W,H} \|V - WH\|^2 \tag{3}$$

performing iteration on two matrices W and H by using a gradient descent method:

$$W_{ik} \leftarrow W_{ik}\frac{(VH^T)_{ik}}{(WHH^T)_{ik}} \tag{4}$$

$$H_{kj} \leftarrow H_{kj}\frac{(W^TH)_{kj}}{(W^TWH)_{kj}} \tag{5}$$

where i has a range of [1,m], j has a range of [1,n], and k has a range of [1, r];

ending the iteration, when the error distance R is less than a threshold or the number of iterations reaches a maximum iteration number, wherein the matrix W obtained at the end of the iteration represents the muscle weight matrix in the muscle synergy pattern, and the matrix H represents the activation degree matrix in the muscle synergy pattern;

the number r of muscle synergies is determined by a difference VAF between a reconstructed matrix Vr and an original matrix V:

$$V_r = WH \tag{6}$$

$$VAF = 1 - \frac{\sum_{i,j}(V - V_r)^2_{i,j}}{\sum_{i,j}V^2_{i,j}} \tag{7}$$

when an average value of the VAF in each motion period is greater than a set threshold, ris determined as a current number of muscle synergies; and performing maximum normalization on the analyzed matrix W, and analyzing similarity of the matrix W in each period by using a correlation coefficient p, which is expressed as:

$$p(W1, W2) = \frac{r\sum_{c=1}^{r} W1_c W2_c - \sum_{c=1}^{r} W1_c \sum_{c=1}^{r} W2_c}{\sqrt{r\sum_{c=1}^{r} W1_c^2 - \left(\sum_{c=1}^{r} W1_c\right)^2}\sqrt{r\sum_{c=1}^{r} W2_c^2 - \left(\sum_{c=1}^{r} W2_c\right)^2}} \tag{8}$$

where W1 and W2 represent muscle weight matrices W for two different action periods, respectively, c represents a column in the corresponding matrix W with a range of [1,r], a plurality of matrices are selected by comparing the correlation coefficient p for averaging, to obtain a weight ratio relationship of a plurality of muscles of the healthy side limb under different muscle synergy patterns;

performing maximum normalization on analyzed activation degree matrix H.

12. The electronic device according to claim 11, wherein the Step S3 comprises:

S3.1: fitting the signal which changes with time with respect to the extracted angle signal, comprising:

preprocessing an original angle signal of the healthy side limb to eliminate possible noises and abnormal values, constructing a fitting function θ(t) to indicate a fitting relationship between the angle and time, and selecting an appropriate period to fit the angle signal, which is expressed as follows:

$$\theta(t) = a_1\sin(\omega t) + b_1 \tag{9}$$

where $a_1$ and $b_1$ are constants to be solved, t is time, and ω is angular frequency;

using a least square method to estimate parameters of the fitting function θ(t), and minimizing an error S1 between an actual value and the fitting function θ(t) by optimizing values of $a_1$ and $b_1$, which is expressed as follows:

$$S_1 = \sum_{i=1}^{n}(y_i - a_1\sin(\omega t_i) + b_1)^2 \tag{10}$$

where $y_i$ represents the actual value of the angle signal;

S3.2: fitting the signal which changes with time with respect to the extracted angular velocity signal, comprising:

preprocessing an original angular velocity signal of the healthy side limb to eliminate possible noises and abnormal values, constructing a fitting function $\theta_1$(t) to indicate a fitting relationship between angular velocity and time, and selecting an appropriate period to fit the angular velocity signal, which is expressed as follows:

$$\theta_1(t) = a_2\sin(\omega t) + b_2 \tag{11}$$

where $a_2$ and $b_2$ are constants to be solved, t is time, and ω is angular frequency;

using a least square method to estimate parameters of the fitting function $\theta_1$, and minimizing an error S2 between an actual value and the fitting function $\theta_1$ by optimizing values of $a_2$ and $b_2$, which is expressed as follows:

$$S_2 = \sum_{i=1}^{n}(y_i' - a_2\sin(\omega t) + b_2)^2 \tag{12}$$

where $y'_i$ represents an actual value of the angular velocity signal, and i represents a sampling point in a range of [1,n];

S3.3: according to characteristic that a muscle activation degree curve has a plurality of peaks, using a Gaussian distribution model to fit the curve to obtain a fitting relationship G(h) between the activation degree and time, which is expressed as follows:

$$G(h) = \sum_{i=1}^{k}\omega_i\phi\left(t; \mu_i, \sigma_i^2\right) \tag{13}$$

where t corresponds to an abscissa in the muscle activation degree, k represents a number of Gaussian distributions, $\omega_i$ represents a weight of an i-th Gaussian distribution, $\phi(h; \mu_i, \sigma_i^2)$ represents a probability density function of the Gaussian distribution, ui represents a mean value of the i-th Gaussian distribution, and $\sigma_i^2$ represents a variance of the i-th Gaussian distribution;

S3.4: according to the relationship θ(t) between the angle and time obtained in S3.1 and the relationship G(t) between the activation degree and time obtained in S3.3, constructing a mapping relationship between the activation degree and the angle;

calculating a derivative of θ(t) and G(t) to obtain θ'(t) and G'(t), and obtaining a corresponding relationship G(θ) between the activation signal and the angle:

$$\frac{dG}{d\theta} = \frac{dG}{dt} \cdot \frac{dt}{d\theta} = \frac{G'(t)}{\theta'(t)} \quad (14)$$

$$G(\theta) = \int \frac{G'(t)}{\theta'(t)} dt \quad (15)$$

performing linear interpolation on angle sampling to match the angle sampling with signal sampling frequency, considering that a sampling frequency of the angle is lower than that of the signal;

S3.5: in the relationship G(θ), selecting a corresponding angle range in which the activation signal is greater than the activation threshold a as an angle range $\theta_r$ in which the muscle synergy pattern is activated.

13. The electronic device according to claim 12, wherein the Step S4 comprises:

S4.1: according to the angle signal fitting function θ(t) obtained in S3.1, solving a maximum angle value of the healthy side limb in different motion periods, and setting the maximum motion angle of the lower limb rehabilitation instrument;

S4.2: according to the angular velocity signal fitting function $\theta_1(t)$ obtained in S3.2, setting a motion speed and a motion period of the lower limb rehabilitation instrument, such that the lower limb rehabilitation instrument works according to the motion model of the healthy side limb of the same individual;

S4.3: setting a frequency and a pulse width of the electric stimulator;

S4.4, setting proportions of electric stimulation intensities of channels of the electric stimulator, setting muscle M with a maximum weight in the muscle weight matrix W to have a maximum stimulation intensity according to the muscle weight matrix W obtained in Step S2, and setting stimulation intensities of other muscles one by one according to formula (16);

$$\frac{S_M}{S_i} = \frac{W_M}{W_i} \quad (16)$$

where $S_M$ represents a stimulation intensity of the muscle M; $S_i$ represents a stimulation intensity of a muscle i, in which i≠M; $W_M$ represents a muscle weight of the muscle M; $W_i$ represents a muscle weight of the muscle i;

S4.5: according to the corresponding relationship G(θ) between the muscle activation degree and the angle obtain in S3.4, starting the electric stimulator with set parameters when the motion angle falls within the angle range $\theta_r$ in which the muscle synergy pattern is activated during operation of the low limb rehabilitation instrument, wherein the electric stimulator continuously works, and when the motion angle does not fall within the angle range $\theta_r$ in which the muscle synergy pattern is activated, the electric stimulator is stopped.

14. The electronic device according to claim 13, wherein the Step S4.3 comprises selecting a lowest frequency capable of activating lower limb muscles of the individual as a stimulation frequency of the electric stimulator, and selecting 50 μs as a pulse width of the electric stimulator.

15. A non-transitory machine-readable storage medium, wherein the machine-readable storage medium stores machine-executable instructions, which, when being called and executed by a processor, cause the processor to implement the method according to claim 1.

16. The non-transitory machine-readable storage medium according to claim 15, wherein the preprocessing the surface electromyographic signal in Step S1 is as follows: performing power frequency removal filtering, band-pass filtering, rectification processing and low-pass filtering on the acquired surface electromyographic signal in sequence to obtain an electromyographic signal envelope.

17. The non-transitory machine-readable storage medium according to claim 15, wherein the preprocessing the motion posture signal in Step S1 is as follows: analyzing the acquired motion posture signal, segmenting the signal according to the motion segments, and extracting motion angle information and motion speed information of a lower limb.

18. An electric stimulation control system based on inspiration of healthy side lower limb muscle synergy, comprising:

a data acquiring and preprocessing module, configured to acquire a surface electromyographic signal and a motion posture signal of a healthy side limb of an individual during an action period; preprocess the signals and segment the signals according to a-motion segments of the action period to obtain a set of electromyographic signal data and a set of motion posture data;

a healthy-side-limb motion model constructing module, configured to analyze, by using a muscle synchronous synergy extraction algorithm, the obtained electromyographic signal of the healthy side limb to obtain a muscle synergy pattern between muscles of the healthy side limb;

an affected-limb motion model constructing module, configured to fit, for the motion posture data, an angle signal and a motion speed signal in a motion process as a motion model of the healthy side limb of the same individual, and map the obtained muscle synergy pattern to a stable angle space for avoiding time-varying influence, to obtain a motion guidance model of the affected limb of the same individual; and an electric stimulation controlling module, configured to set, according to the motion guidance model, a maximum motion angle, a motion speed, and a motion period of a lower limb rehabilitation instrument connected to the individual, and set, according to the motion guidance model, proportions of electric stimulation intensities of channels of an electric stimulator, which is contained in the lower limb rehabilitation instrument and has control points attached to skin surface of affected side lower limb muscles of the individual, and an angle range for starting the electric stimulator, such that during the low limb rehabilitation instrument being working according to the motion model of the healthy side limb of the individual, the electric stimulator is started when a motion angle of the low limb rehabilitation instrument falls within the angle range in which the muscle synergy pattern is activated, and when the motion angle does not fall within the angle range, the electric stimulator is stopped.

19. An electronic device, comprising a processor and a memory, wherein the memory stores machine-executable instructions capable of being executed by the processor, and the processor executes the machine-executable instructions to implement the system according to claim 18.

20. A non-transitory machine-readable storage medium, wherein the machine-readable storage medium stores machine-executable instructions, which, when being called and executed by a processor, cause the processor to implement the system according to claim 18.

* * * * *